United States Patent [19]

McAleer et al.

[11] 4,028,190
[45] June 7, 1977

[54] APPARATUS FOR PREPARING ISOLATED CELLS FROM TISSUE

[75] Inventors: William J. McAleer, Ambler; William M. Hurni, North Wales, both of Pa.

[73] Assignee: Merck & Co., Inc., Rahway, N.J.

[22] Filed: Nov. 17, 1975

[21] Appl. No.: 632,610

Related U.S. Application Data

[63] Continuation of Ser. No. 521,922, Nov. 7, 1974, abandoned.

[52] U.S. Cl. .................................. 195/127; 195/1.8; 241/277; 233/27
[51] Int. Cl.$^2$ .......................................... C12K 9/00
[58] Field of Search ..................... 195/127, 1.8, 1.7

[56] References Cited

UNITED STATES PATENTS 3,104,225  9/1963  Benedetto ........................... 233/28

FOREIGN PATENTS OR APPLICATIONS 1,356,794  6/1974  United Kingdom ............... 195/127

OTHER PUBLICATIONS

J. Appl. Chem. Biotechnol. vol. 22, pp. 335–341 (1972).

*Primary Examiner*—Alvin E. Tanenholtz
*Attorney, Agent, or Firm*—Donald J. Perrella; J. Jerome Behan

[57] ABSTRACT

An apparatus and a method for preparing live, sterile cells from tissue are disclosed which enable high yields of viable isolated cells to be obtained with a greatly reduced possibility of contamination of the cells during the process. The apparatus and method allows one to truly mass manufacture isolated cells as contrasted to a small hand operation requiring many hours and dozens of people. The improved apparatus of the invention comprises a shredder device which mechanically shreds the tissue into small pieces of high surface to volume ratio, a processing vessel in which the shredded tissues are contacted with an enzyme solution to break down the intercellular material and thereby separate the cells one from the other and a means for separating the cells from the enzyme solution. Preferably, the means for separating the cells from the enzyme solution is a flow centrifuge which has been specifically designed to reduce shear force inside the bowl during operation. Also disclosed is a process for shredding tissue employing a plurality of moveable blade elements and at least a corresponding number of separated fixed elements. Interposing the tissue between the fixed and rotating elements and then driving the moveable blade elements through the spaces defined by adjacent fixed elements results in the tissue being shredded into small pieces of high surface to volume ratio. This in turn optimizes surface area for contact between the shredded tissue and the enzyme solution. In addition, a completely closed process is disclosed for obtaining cells from the tissue comprising the steps of sequentially shredding the tissue, contacting the shredded tissue at a controlled temperature with an enzyme solution to break down the intercellular material and then separating the isolated cells from the enzyme solution.

11 Claims, 8 Drawing Figures

APPARATUS FOR PREPARING ISOLATED CELLS FROM TISSUE

RELATED APPLICATIONS

This application is a continuation of application Ser. No. 521,922, filed 7 Nov. 1974, now abandoned.

BACKGROUND OF THE INVENTION

1. Field of the Invention

The present invention generally relates to a process and apparatus for obtaining viable sterile primary cells from tissue, and more particularly relates to a semiautomated process and apparatus useful for obtaining live, sterile, tissue cells from chick or duck embryos or the like. In addition, the present invention relates to an improved centrifuge means useful in separating enzymatically isolated cells from a liquid in which they are carried, and further relates to an improved shredding device for mechanically breaking down the tissue prior to digestion with an enzyme. The present invention also relates to a process for shredding the tissue.

2. Description of the Prior Art

The obtaining of cells from tissue, as for example chick or duck embryos, is known per se and produces materials which are useful in biochemical or immunological research. Typically, such tissue cells are obtained by breaking eggs which contain embryos and extracting the partially developed embryos therefrom. The embryos are then cut up into small pieces and washed in a washing solution. Following the washing step, the minced embryos are mixed for a period of time at a controlled temperature with an enzyme such as trypsin, which breaks down the intercellular material and releases the individual cells or groups thereof. Following this enzyme digestion step, the cells are separated from the enzyme solution by any suitable means such as by spinning the mixture in a bucket type, fixed volume, centrifuge which separates the solid from the liquid material. The cellular material recovered from the centrifuge may then be maintained alive until it is used for culture purposes or the like.

The prior art teaches a manual technique for recovering cells from tissue such as chick or duck embryos. The process, for example, involves hand cutting or mincing the whole embryo, such as with scissors, followed by washing the same with the washing liquid, thereafter mixing the minced pieces of embryo with the enzyme (such as trypsin) in a flask, with the contents being stirred therein with the use of, for example, a magnetic stirrer device. After a suitable amount of time in which the minced embryos are digested with the enzyme at a controlled temperature, the resulting mixture is poured into a glass flask and subjected to centrifugation to separate the solid cellular material from the liquid, after which the liquid is decanted from the glass flask. The remaining solid cellular material may then be mixed with a nutrient to maintain the cellular material viable for a suitable period of time prior to use.

The prior art has recognized that the production of large amounts of tissue cells from chick embryos by manual techniques is difficult and expensive. Thus, F. C. Belton and B. P. Garriock (in "A Semi-Automatic Method for the Production of Primary Cell Suspensions," Journal of Applied Chemistry and Biotechnology, Volume 22, pages 335–341 [1972]) have suggested a tissue production complex useful for processing chick embryo suspensions. The apparatus described in that article consists of a ram-type cutter for mincing the washed whole embryos, a processing unit in which enzyme digestion may be conducted, and a plurality of bucket type centrifuges for separating the cellular material from a solution thereof. However, the system disclosed by Belton and Garriock lacks the degree of automation of the present invention. Further, for reasons to be explained hereinafter, that prior system is incapable of obtaining the high cell yields which the present invention obtains.

Obviously, any open system for recovering the tissue cells is difficult and time consuming and the possibility of contamination of the cells is substantial. For a general review of various techniques used in recovering live tissue cells, reference is here made to *Cells and Tissues in Culture*, edited by E. N. Willmer, Academic Press, Inc., New York (1965).

Despite the teachings of the prior art, there is a need for a process and apparatus useful for obtaining the tissue cells which is capable of handling large numbers of embryos while producing good yields with minimal handling of the same during processing and thereby decreasing the possibility of contaminating the cells during the operations.

SUMMARY OF THE INVENTION

It is therefore a primary object of the present invention to provide a process and apparatus for obtaining live cells from tissue.

It is a further object of the present invention to provide a semi-automated apparatus for obtaining live tissue cells from embryos which can process large numbers of embryos and reduces handling of the same during processing and thereby reduces the possibility of contamination of the cell slurry produced.

It is yet a further object of the present invention to provide a semi-automated apparatus for obtaining live, sterile tissue cells from embryos which permits higher yields of viable cells per gram of embryo processed.

It is a further object of the present invention to provide an improved centrifuge useful in obtaining higher yields of viable cells.

It is still a further object of the present invention to provide an improved shredding device for cutting the embryos which not only shreds the same but strands the tissue enabling higher yields of viable cells to be obtained.

It is yet a further object of the present invention to provide a process for shredding the embryos and a complete process for extracting the cells from the embryos.

It is yet a further object of the present invention to provide a process which can conveniently process large numbers of embryos.

Other objects, features and advantages of the invention will become apparent from the ensuing description.

In summary, the present invention includes the following embodiments:

A. A semi-automated apparatus for obtaining high yields of tissue cells including a shredder device which shreds the tissue in addition to breaking the embryo into small pieces, a processing vessel for the enzyme digestion of the shredded embryos and a means (i.e., a centrifuge, a filter or the like) for separating the solid cellular material from the liquid enzyme solution. preferably the means for separating the solid cellular material from the liquid enzyme solution is a flow centrifuge which is specifically designed to substantially reduce the shearing forces acting on the cells during separation.

B. A process for shredding the embryos comprising passing the embryos through cutting means which shreds the embryonic tissue in addition to breaking up the embryos, thereby increasing the surface area subject to enzyme digestion and increasing the yield of viable cells obtained.

C. A shredder device for shredding the embryos prior to enzyme digestion which comprises a plurality of movable blade elements and at least a corresponding number of separated fixed elements wherein the movable blade elements are adapted to be driven through the spaces defined by adjacent fixed elements thereby shredding an embryo disposed between the movable and fixed elements, wherein the clearance between the movable and fixed elements is such that the embryonic tissue is shredded to expose a greater surface area to enzymen digestion.

D. A centrifuge for separating cells from the liquid enzyme solution which includes a rotatable bowl provided with means for reducing the shear forces to which the cells are subjected during separation.

E. A process for extracting the cells including the steps of sequentially shredding the embryos, contacting the shredded embryos at a controlled temperature with an enzyme solution to break down the intercellular material, and then separating the solid cellular material from the liquid enzyme solution without subjecting the cells, during separation, to high shear forces. Preferably the separation is carried out by a flow centrifuge.

BRIEF DESCRIPTION OF THE DRAWINGS

FIG. 7 is an exploded view showing the interior construction of the elements of the bowl assembly of the centrifugal separator of FIG. 6.

FIG. 8 is a view illustrating the spinner vane additions constituting one of the improvements of the centrifugal separator of the present invention.

DESCRIPTION OF THE PREFERRED EMBODIMENTS

The system of the present invention is especially useful in obtaining live, sterile cells from tissue such as chick or duck embryos in high yields. However, the system of the present invention is also useful in obtaining live sterile tissue cells and cell suspensions from many different sources. For purposes of ease of illustration only, the present invention will be described by reference to its preferred embodiment although those skilled in the art should be aware of the broader implications of the present invention and the broader utility.

In obtaining live, sterile tissue cells from chick embryos, it is conventional to first candle the eggs to determine the presence of a chick embryo. Any conventional apparatus can be used for this purpose, and the means for candling the eggs forms no part per se of the present invention. In addition, the means and technique used for incubating the eggs forms no part per se of the present invention, nor does the particular method of removing the embryos from the eggs. Those skilled in the art are aware of conventional apparatus and known techniques for accomplishing these purposes, and no effort will be made here to describe the same.

Figure 1:
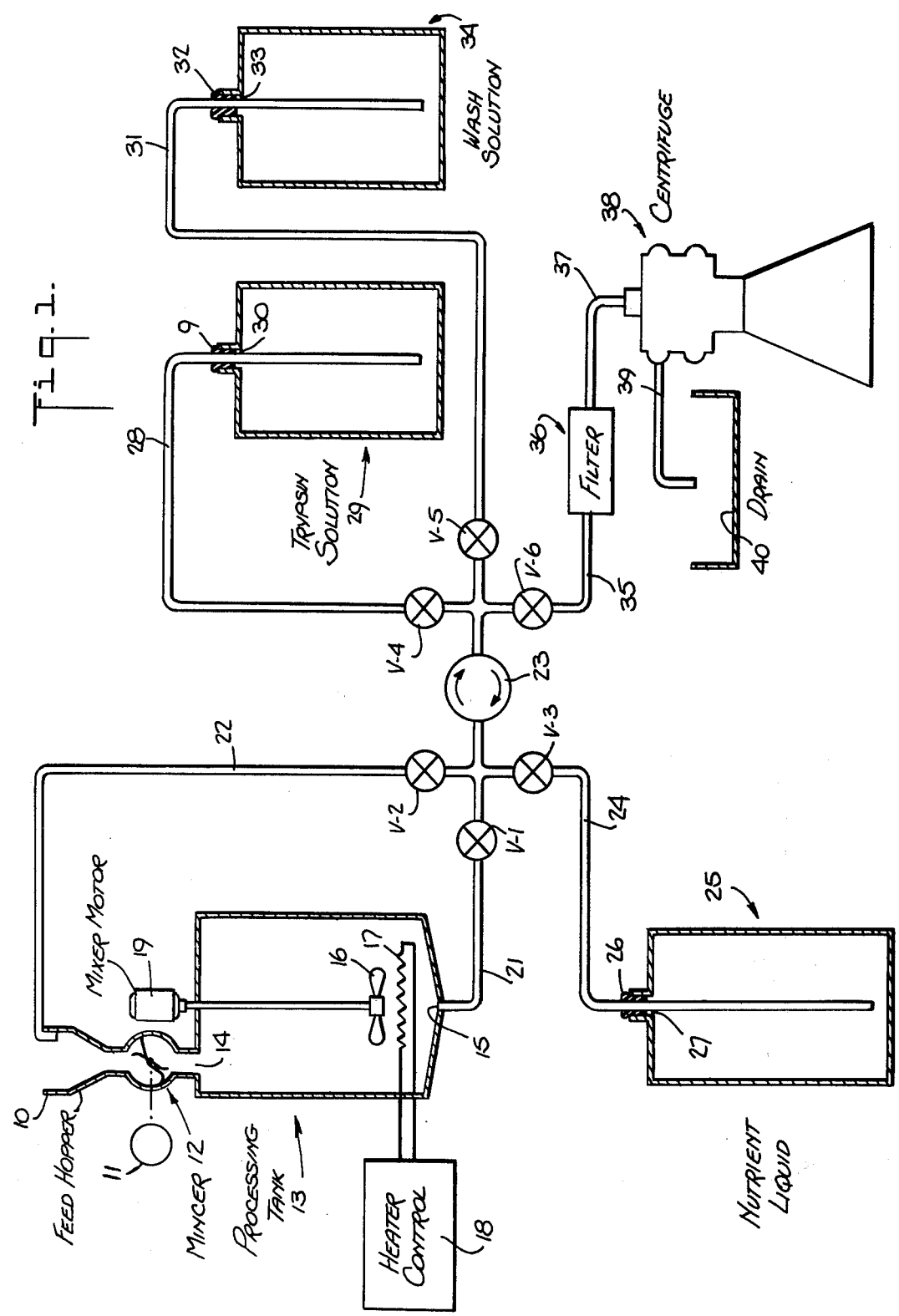
FIG. 1 is a schematic illustration of a tissue cell recovery system in which the present invention is embodied.

Referring now to FIG. 1, a schematic illustration of the entire system of the invention is illustrated. Specifically a feed hopper 10 is provided for feeding partially incubated chick embryos into the shredder 12 (which will be described in detail below). A motor 11 is provided for driving the cutting element of the shredder 12. The shredded embryos pass downwardly through an exit 14 of the shredder and into a processing tank 13, the latter being provided with a mixer 16 driven by a motor 19, and a heating element 17 whose temperature may be controlled with a control means 18. In addition to the feeding of embryos into the feed hopper 10, a wash solution from a tank 34 is also fed thereto simultaneously with the chick embryos. The wash solution from tank 34 is fed to the hopper 10 as follows. A conduit means 31 is inserted into the tank 34 through an opening 33 therein and the tank is sealed by means of a stopper means 32. Any other arrangement which permits the solution contained in the tank to be withdrawn therefrom may also be utilized.

A reversible, variable speed tubing pump means 23 is provided for pumping the various fluids and solutions throughout the apparatus. In order to feed the wash solution through a conduit means 22 into the hopper 10, valves V-1, V-3, V-4 and V-6 are closed and valves V-2 and V-5 are opened, in order to permit the pump means 23 to force the wash solution from the tank 34 into the feed hopper 10 along with the chick embryos.

The shredded embryos are washed in the processing tank 13 with the wash solution, which is conveniently a sterile saline solution. After the minced embryos have been sufficiently washed, the valves V-1 and V-5 are opened and the remaining valves closed, and the pump means 23 is used to remove the wash solution from the processing tank 13 through the exit 15 thereof and thereafter through the conduit means 21, 31 back into the wash container means 34.

Following the washing operation a trypsin solution is fed to the processing tank 13 from a tank 29. A conduit means 28 is inserted into an opening 30 of the tank 29 and is sealed via a stopper means 9. By opening the valves V-4 and V-1, and closing all other valves, the trypsin solution from the tank 29 is pumped through the pump means 23 and the conduit means 21 into the processing tank 13 through the opening 15 thereof. The shredded embryos and the trypsin solution are mixed and heated in the processing tank 13 for a period of about 2 hours at a controlled temperature of about 37° C during which the shredded embryos are digested by the trypsin. Following this enzyme digestion step, which is designed to break down the intercellular material in the shredded embryos and to free the individual cells or groups of cells, the trypsin/embryo/cell mixture is fed to the centrifuge 38 by opening the valves V-1 and V-6, closing all the other valves and pumping the mixture to the centrifuge. The filter means 36 removes undesirable materials such as undigested tissue, etc.; and the centrifuge 38 (which will be described below in greater detail) separates the solid cellular material from the trypsin solution, the latter being fed to the drain 40 via the conduit 39.

In order to assure that all of the trypsin is displaced from the centrifuge, a nutrient liquid is fed from a tank 25 to the centrifuge 38 by opening the valves V-3 and V-6 and closing all other valves. A conduit means 24 is inserted into an opening 27 of the tank 25 and is sealed via a stopper means 26. Pump 23 is employed to force the nutrient liquid from the tank 25 into the centrifuge 38. The nutrient liquid drains out of the centrifuge via the conduit 39 into the drain 40, and the solid cellular material may then be removed from the bowl of the centrifuge.

The various tanks, conduit means, valves, pump means, etc. as shown in FIG. 1, should be formed of a material which lends itself to sterilization. For example, the tanks may be formed of glass and may be autoclaved prior to use for a period of about 1 hour at a temperature of about 121° C in order to sterilize the same. The solutions which are fed into the various tanks are of course sterile, and since the system shown in FIG. 1 is closed and may be operated without manual handling of the embryos or the various solutions, the risk of contamination of the cell slurry produced is greatly reduced. In addition, due to the design of the shredder 12 and the centrifuge 38, the yield of viable cells obtained is very high based on the weight of embryos fed into the system.

The heater control 18 of the processing tank 13 may be any conventional control device which can regulate the temperature of the heating element 17. Similarly, any conventional reversible and variable speed pump means can be employed as the pump 23, as long as it can be sterilized prior to incorporation into the system. Similarly, if the various materials must flow through the valves, the latter must be capable of sterilization, or exterior valve means can be employed, such as simple clamping devices which can be used to regulate flow through flexible tubing. The filter 36 removes coarse materials from the solutions or mixtures flowing through the conduit 35 to the conduit 37 and the centrifuge 38. For example, the filter 36 may comprise a millipore filter using the filter support pad as the filtering agent.

The present invention does not reside per se in the particular materials used in the wash solution, trypsin solution, or nutrient liquid, and generally any conventional material can be used for these purposes with those skilled in the art being able to select appropriate materials. Reference is made to E. N. Willmer, supra, and to L. M. Rinaldini, "The Isolation of Living Cells from Animal Tissues," *International Review of Cytology*, Vol. 7, page 587 et. seq. (1958), for a disclosure of materials used for these purposes, the disclosures of the aforementioned being expressly incorporated herein by reference. A typical example of a trypsin solution which may be used in TRIS trypsin. The wash solution, for example, may be Hanks Balanced Salt media and the nutrient solution may be formed by adding 10% of FCS to Medium 199.

Figure 2:
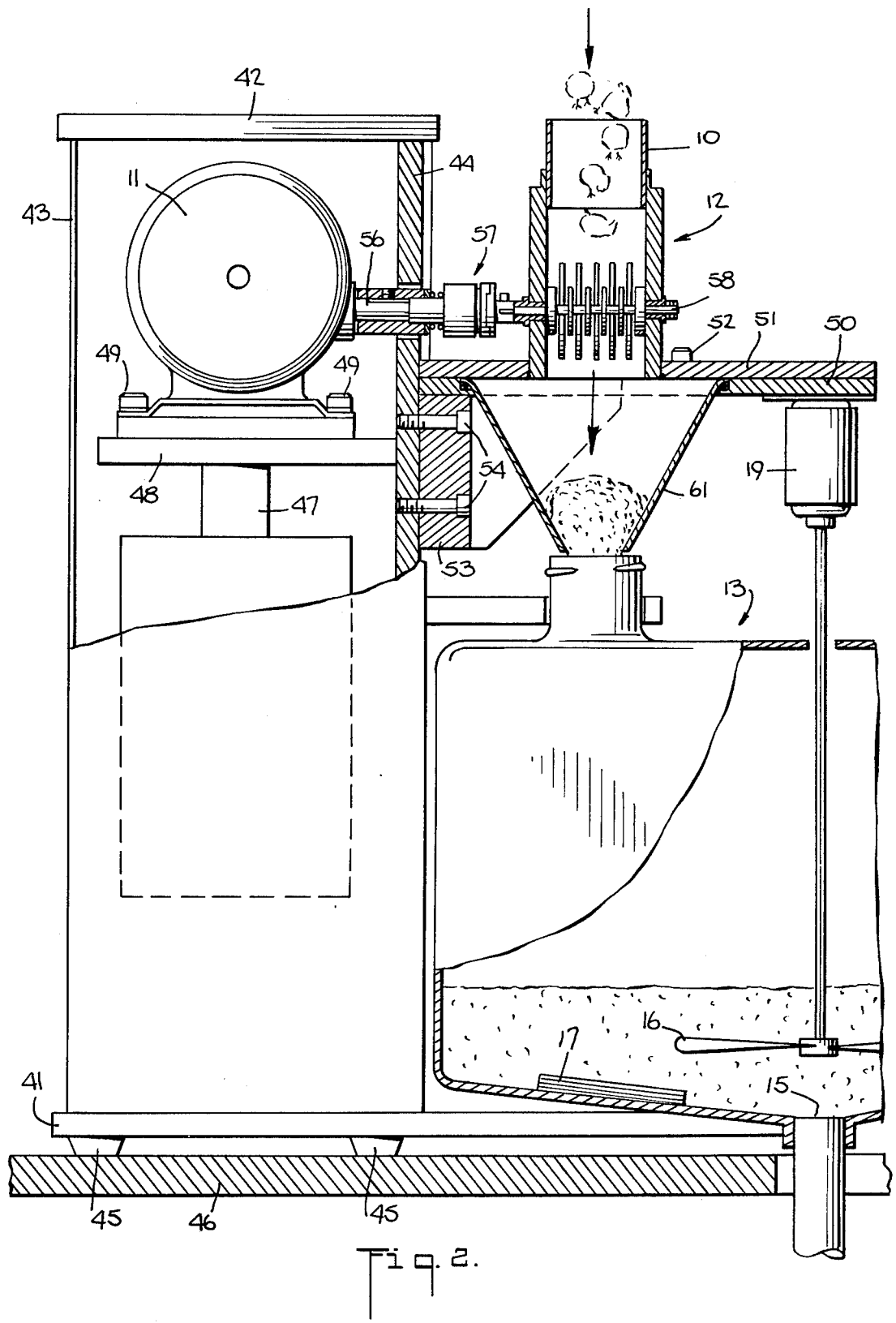
FIG. 2 is a side elevational view, partly in cross-section of a shredding device forming one element of the system of FIG. 1.
Figure 3:
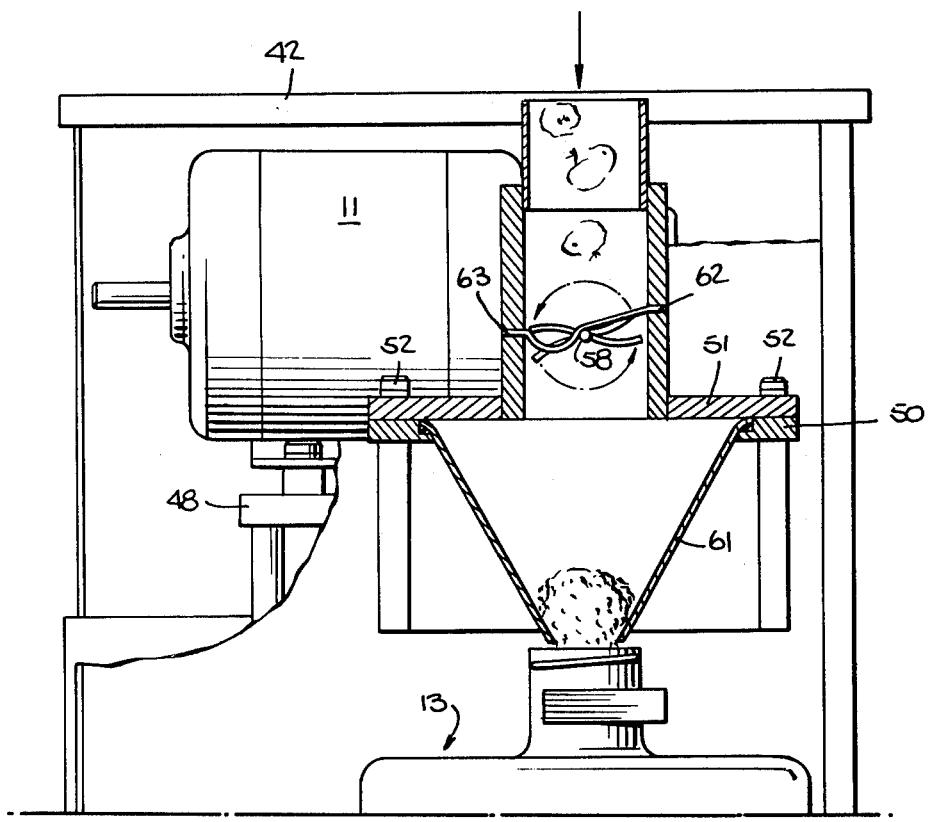
FIG. 3 is another side elevation view, partly in section of the shredding device of FIG. 2.
Figure 4:
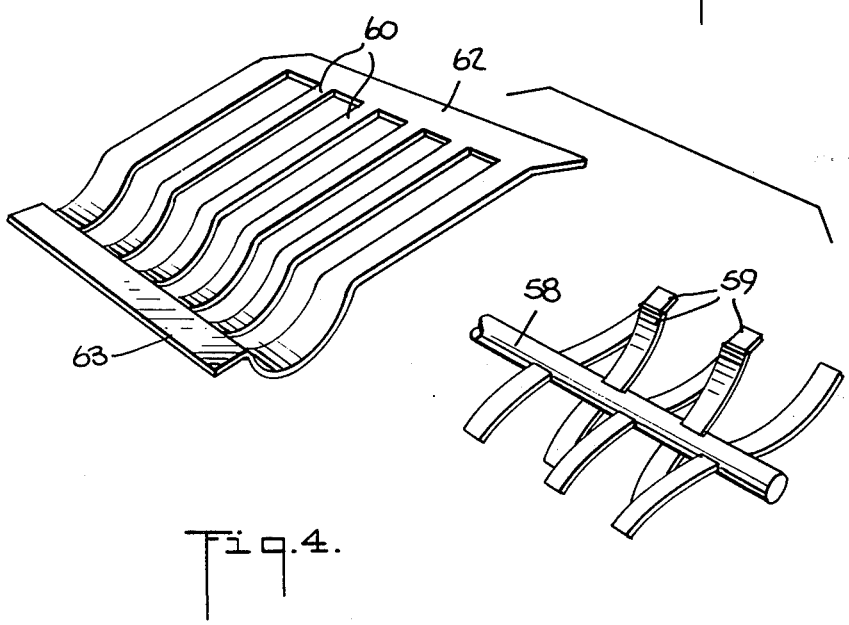
FIG. 4 is an exploded view showing the cutting members of the shredding device of FIGS. 2 and 3.

Referring now to FIGS. 2, 3 and 4, the shredder 12 is shown in greater detail. A housing defined by a lower frame 41 and an upper frame 42 and sidewalls 43 and 44 is supported on legs 45 on a support means 46, such as a table. Attached to the lower frame member 41 is a support member 47 which in turn supports a plate 48. A motor 11 is attached by bolts 49 to the plate 48.

The shredder 12 is supported on a plate 51 which in turn is secured to a plate 50 by bolts 52. Plate 50 is secured to or is integral with a block means 53 which in turn is secured to the sidewall 44 by bolts 54. A motor is used for rotating the mixing device 16, the particular means of support not being shown.

The shredder device of the invention not only cuts apart the embryos into small pieces but also, by virtue of the shape and design of its cutting elements, it shreds the embryonic tissues to separate the cells and to expose a greater surface area for enzyme digestion. More specifically, the essential features of the shredder comprise at least one set of a plurality of driven movable blade elements and at least a corresponding number of fixed blade elements. By interposing an embryo between the movable and fixed blade elements and by driving the movable blade elements through the spaces defined between adjacent fixed elements, the embryo is shredded into small pieces and the tearing action effected between different pairs of movable and fixed blade elements, due to the small clearance between the two, shreds the tissues of the embryo. As a result of the shredding the tissue is separated and a greater tissue surface area is available for contact with the enzyme solution which results in a greater number of viable cells being obtained. The clearance between the fixed and movable blade elements is ordinarily about one thirty-second inch to about three sixty-fourth inch, preferably on the order of one thirty-second inch although those skilled in the art will realize that the clearance may vary depending on various factors.

The shredder device 12, as is shown in FIGS. 2, 3 and 4 conveniently comprises a series of rotary blades of particular shape which are capable of being rotated about an axis or shaft 58 by means of a motor 11. More specifically, the motor 11 is adapted to rotate a shaft 56 and, in turn, the shaft 58 through clutch 57. Fixed and stationary members of particular shape 60 (best seen in FIG. 4) are arranged in spaced apart relationship to define spaces therebetween through which the blades 59 pass when rotated.

As shown in FIG. 4, which is an exploded view of the interior elements of the shredder, the fixed elements 60 are secured to the sidewalls of the shredder by portions 62 and 63 which are embedded in the sidewalls (see FIG. 3). The movable blades 59 rotate in the direction shown in FIG. 3 when shredding embryos. They can be reversed. Plate 50 also supports a conical funnel means 61 disposed below the exit of the shredder 12. Below the funnel means 61 is disposed the processing tank 13. The heating element 17 is provided in the lower portion of the processing tank 13, the heating element being schematically shown. The means for heating the same and controlling the temperature are not shown. As the embryos are fed through the feed hopper 10 to the shredding device, the rotating blade members 59 finely shred the embryos which pass downwardly through the shredder, into the funnel means 61 and thence into the processing tank 13, where the above described operations occur. Due to the shredding action between the rotatable blades 59 and the fixed elements 60, and due to the clearance between the same, the embryo is finely shredded. This shredding, combined with the design of the centrifuge, greatly increases the yield of viable cells which are obtained with the apparatus of the present invention.

The use of a centrifuge for separating the solid cellular material from the liquid enzyme solution is known. It has been believed that high G forces can damage the live cells during the separation process. Contrary to this prior art belief, it has now been discovered that high G-forces (approximately 10,000G) may be tolerated in cell separation and that different forces, namely shear forces, have been responsible for primary cell damage in the flow centrifuge. Thus, according to the present invention cell yields are improved even at high centrifuge speeds by means of novel centrifuge arrangements which avoid subjecting the cellular material to high shear producing forces.

Figure 5:
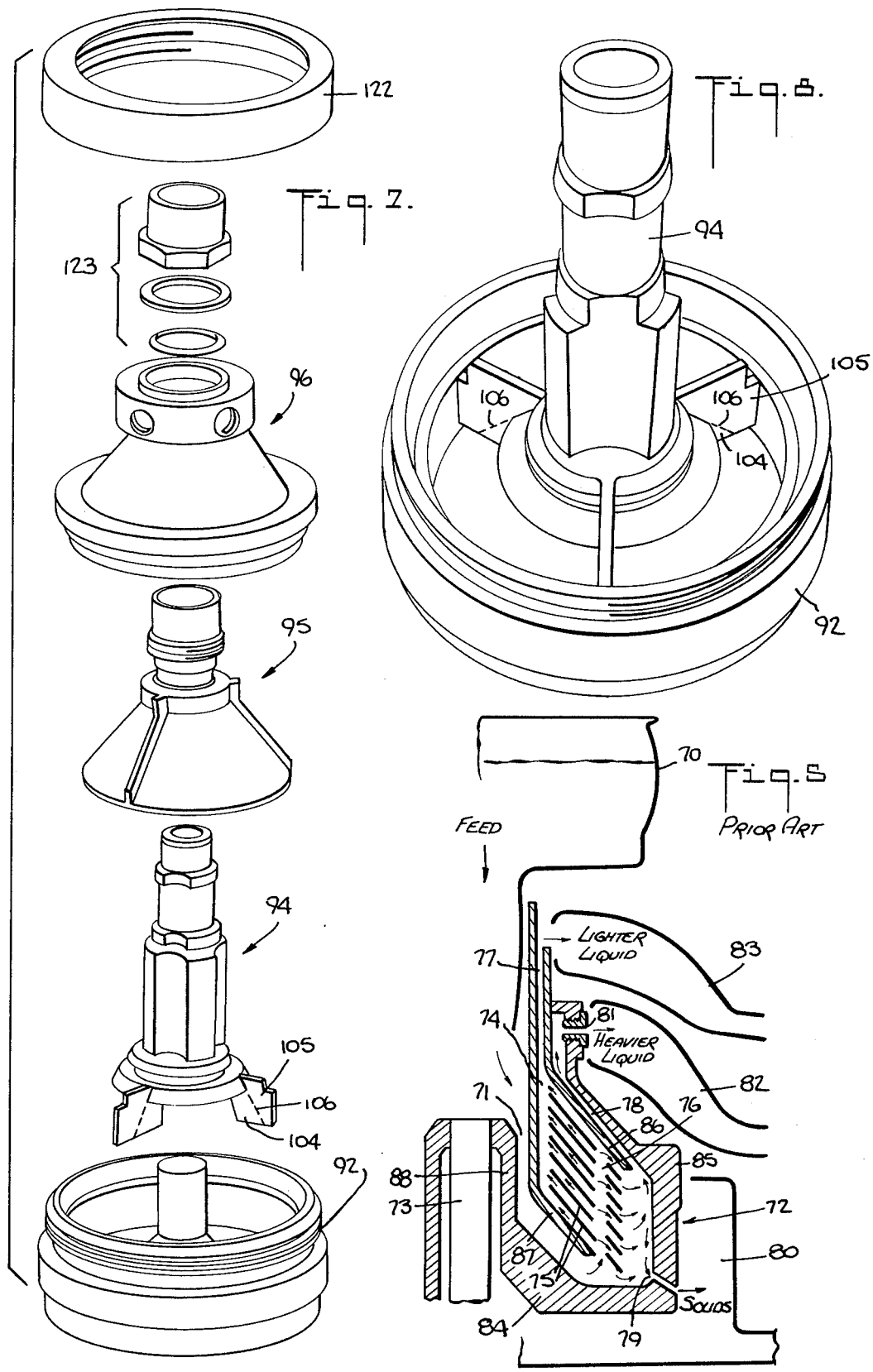
FIG. 5 is a partial elevational view, partly in cross-section of a centrifugal separator in the system of FIG. 1.

Referring to FIG. 5, the bowl arrangement of a conventional prior art flow centrifuge is illustrated, specifically a type which is used to separate a liquid-liquid-solid mixture, with one liquid being heavier than the other. Essentially, a conventional flow centrifuge comprises a bowl which is rotated at a high rate of speed and has a centrally-disposed feed point, as illustrated at FIG. 5. Specifically, referring to FIG. 5, a bowl unit is generally designated 72 and comprises a bowl shell 84 having an upwardly protruding central portion 88, the latter being provided with a rotatable spindle 73 for rotating the entire bowl 72. A tubular shaft 87 is inserted into the bowl shell 84, the tubular shaft 87 having its bottom portion angled as shown in FIG. 5, and having tapered radially-disposed spinner vanes (not shown) provided at the lowermost portion of the tubular shaft. The tubular shaft defines a space 71 between it and the bowl shell 84. A plurality of intermediate discs 75 (which are conical in shape) are provided surrounding the tubular shaft 87, with suitable spacing means such as ribs (not shown) being provided on each of the intermediate discs to provide separation between each individual disc. The discs 75 are provided with holes 76 which are aligned vertically, as shown in FIG. 5. A top disc 86 is further provided around the tubular shaft overlying the uppermost intermediate disc. No holes are provided in the top disc 86, and a bowl top 85 surrounds the upper portion of the bowl 72 and defines a space 78 between the bowl top 85 and the top disc 86.

Above the bowl assembly is provided a feed cup 70 from which the mixture to be separated is fed axially downwardly into the bowl by gravity. Specifically, the mixture is fed downwardly through the tubular shaft 87, through the space 71 while the entire bowl assembly is being rotated by means of the spindle 73. As the mixture enters the interior of the bowl assembly, it flows outwardly due to centrifugal force and upwardly through the holes 76 provided in the intermediate discs 75. Most of the heavier liquid and the heavy solids are immediately forced outwardly toward the outer edge of the rotating bowl assembly. The lighter liquid is displaced inwardly toward the tubular shaft 87 where further liquid-liquid separation occurs. Specifically, the heavier liquid travels downwardly on the underside of the discs 75 while the lighter liquid moves upwardly along the upper side of the discs 75. The lighter liquid, after passing upwardly through the discs 75, flows through spaces 74 and 77 and along the underside of top disc 86 into a space 83 where it is collected.

At the same time, the heavier liquid, having been forced to the outside of the bowl assembly, flows upwardly along the interior wall of the bowl top 85, over the top disc 86 into a space 78, from which it exits at a port 81 into a collecting area 82 where it may be collected.

All of the solid material collects on the interior wall of the bowl 84, and if the mixture has a high solid content, the solids flow downwardly along the interior wall of the bowl 85, out a port 79 and into an area 80 where they may be collected if desired.

The arrows in FIG. 5 generally indicate the pattern of flow in the interior of the bowl assembly 72. In the conventional flow centrifuge, as noted briefly above, the lowermost portion of the tubular shaft is provided with a plurality of radially-extending tapered spinner vanes which extend from the lowermost portion of the tubular shaft to the bottom of the bowl shell and which are tapered from the tubular shaft toward the bottom of the bowl shell.

The modifications necessary to the above described conventional flow centrifuge to obtain the novel flow centrifuge of the present invention are as follows. Essentially, the modifications include removing all of the intermediate discs 75, blocking off the port 79, blocking off the passageway 78 at its lowermost point, and extending the edges of the spinner vanes out to the circumference of the bowl shell. The latter improvement or modification has been found to reduce the shearing action which otherwise would occur around the edges of the prior art tapered spinner vanes. It has further been found that, contrary to popular belief, the speed of rotation of the bowl assembly may be increased without damaging the cellular material contained therein in view of the spinner vane extensions, since they act to reduce the shear on the cellular material present in the rotating bowl. This enables greatly increased yields of cells to be obtained. In other words, the centrifuge of the present invention is designed to avoid sudden changes in velocity of the cells during centrifugation thereby reducing the shear forces to which the cells are subjected.

Figure 6:
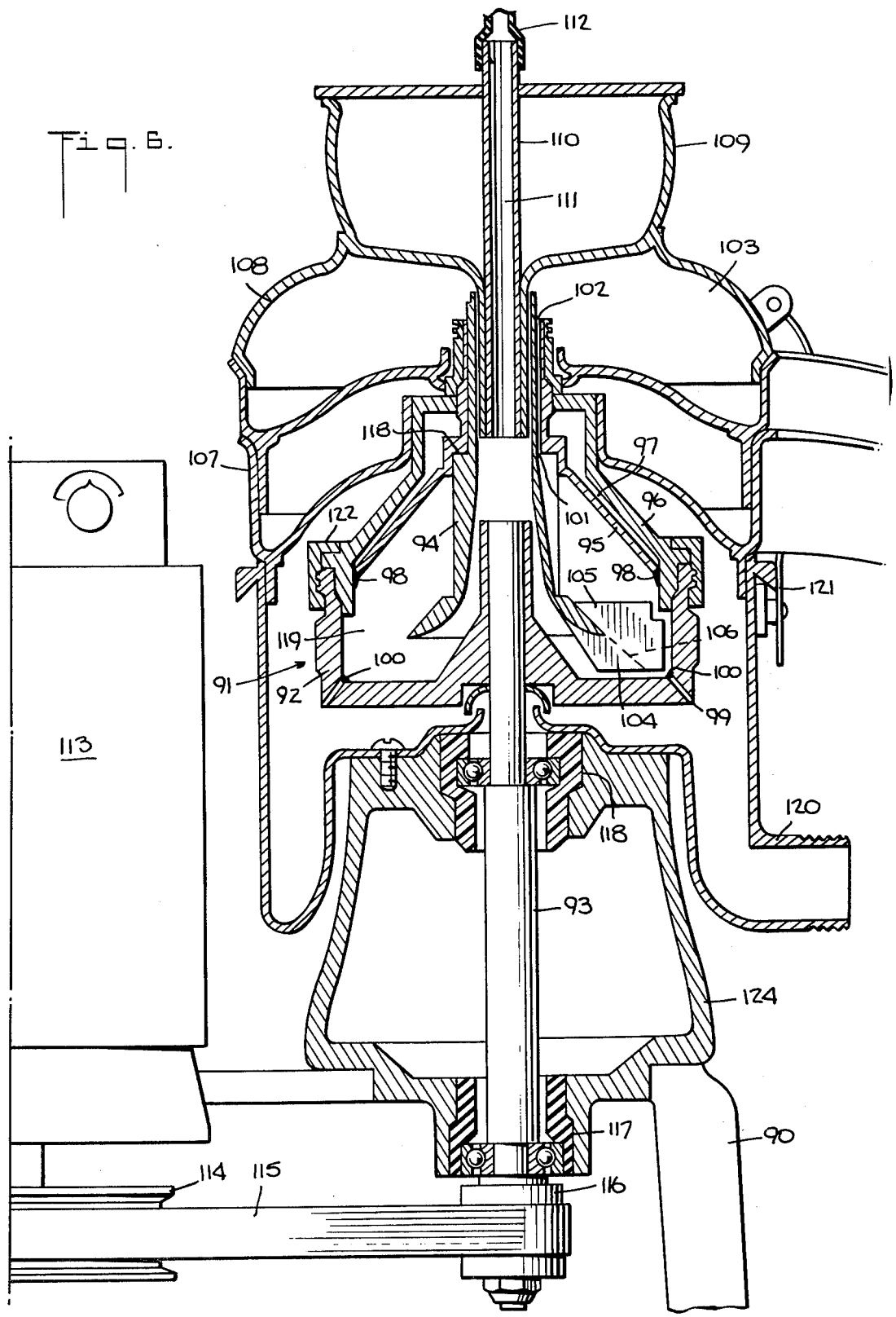
FIG. 6 is a side elevational view, partly in cross-section, of a centrifugal separator used in the system of FIG. 1 and forming one aspect of the present invention.

Referring to FIGS. 6, 7 and 8, the centrifuge used in the system of the present invention will now be described. FIG. 6 is a side view, partly in cross-section, of the centrifuge of the invention. In order to avoid confusion with FIG. 5, different reference numerals will be employed to describe identical parts.

Referring now to FIG. 6, a centrifugal separator device is shown which comprises a base 90 which supports a bowl casing 124 and a motor 113. A bowl assembly generally designated 91 is rotatably supported by a bowl spindle 93 which may be rotated by means of a bottom and a top bearing 117 and 118, respectively. Motor 113 is a variable speed motor preferably, such that the speed of rotation of the bowl assembly 91 may be regulated as desired.

Bowl assembly 91 is rotated by virtue of the fact that a belt 115 is provided around a driven motor pulley 114 and a spindle pulley 116, the latter which is secured to the spindle 93.

Bowl assembly 91 comprises a bowl shell 92 which mounts onto the upper portion of the spindle 93. A tubular shaft 94 is inserted into the bowl shell 92, the upper end of the tubular shaft extending upwardly through the center of the bowl assembly 91. The lower end of the tubular shaft 94 is provided with a plurality of radially-extending spinner vanes, which will be discussed below.

Surrounding the tubular shaft 94 is a top disc 95 which sits on the tubular shaft 94 at a surface 118, thereby providing a space 119 in the interior of the bowl assembly 91. Surrounding the top disc 95 is a bowl top 96 which is secured onto the bowl shell 92 by means of a threaded ring 122 as shown in FIG. 6. A space 97 defined by the top disc 95 and the bowl top 96 is sealed off from the space 119, such as by means of a weld 98, for example.

A further modification is in sealing off a port 99 (which is for solid removal and which corresponds to the port 79 in FIG. 5) at 100, such as by means of a weld, for example. A further modification is in the spinner vane extensions 105. The prior art teaches the provision of tapered spinner vanes 104 and the present invention adds (to spinner vanes 104) the portion designated 105, by, for example, welding the addition 105 to the vane 104 along a line 106. It will be appreciated, therefore, that the spinner vanes of the flow centrifuge of the invention extend substantially to the periphery or circumference of the bowl shell 92 compared to the prior art vanes which are tapered and do not extend to the circumference of the bowl shell 92.

In addition, none of the intermediate discs of the prior art centrifuges are present in the bowl assembly 91 of the invention. (In other words, the intermediate discs 75 of FIG. 5 have been removed from the device shown in FIG. 6.) The extensions 105 contribute to the reduction of shear forces.

On top of the bowl top 96 is provided a bottom cover 107, a top cover 108, and a regulating cover 109. Space 97 would normally connect the space 119 with the interior of the bottom cover 107, but since the space 97 has been sealed at 98, no liquid can enter the bottom cover. However, the liquid which is fed into the space 119 travels along the underside of the top disc 95, into a space 101 and eventually into a space 103 in the upper cover 108 via a port 102. The solid material therefore, is merely collected in the bowl shell 92 since the port 99 has been sealed at 100.

A feeding tube 110 is provided which extends from the exterior of the centrifuge at its top down through the regulating cover 109 and the upper and lower covers 108 and 107 respectively, and into the bowl assembly 91. A conduit means 112 (which compares to the conduit means 37 in FIG. 1) feeds the mixture to be centrifuged to a conduit 110 from which it flows through a space 111 downwardly into the center of the bowl assembly 91, from which it flows between the bowl shell 92 and the tubular shaft 94 into the space 119.

An upper bowl casing 120 is normally provided to collect solid material which would normally be expelled from the bowl shell 92 via the port 99, but which has been sealed at 100. The regulating cover 109, the top cover 108 and the lower cover 107 are removably secured to the upper bowl casing 120 by means of a clamp 121.

In operation, a mixture to be separated is fed downwardly through the space 111 of the conduit 110 into the center of the bowl assembly 91. The mixture then passes between the tubular shaft 94 and the bowl shell 92 into the space 119. The bowl assembly 91 is being rotated by the spindle 93 which in turn is being powered by the motor 113 through the motor pulley 114, the belt 115, and the spindle pulley 116. As the mixture enters the space 119, the cells contained therein are accelerated and forced outwardly toward the circumference of the bowl shell 92. The lighter liquid portion of the mixture, the trypsin solution, is forced upwardly along the circumference of the bowl shell 92 and then along the underside of the top disc 95 into the space 101, out the port 102 and into the space 103 of the top cover 108, from which it may be collected or drained. The seal 98 prevents liquid from entering the space 97, and the seal 100 prevents the solid cellular material from exiting the bowl shell 92 via the port 99, and hence, when the rotation of the bowl assembly 91 is stopped, the solid cellular material remains in the bowl shell 92 and may be recovered therefrom. However, as is noted above, nutrient liquid is passed through the centrifuge before the cells are recovered to assure that all of the trypsin solution has been removed from the centrifuge.

Reference is made to FIG. 7, which is an exploded view of the bowl assembly of the centrifuge of the present invention, where the same reference numerals indicate identical parts as in FIG. 6.

Reference numeral 123 indicates a rubber ring, a washer and a nut, proceeding upwardly, respectively, which is used to securely fasten the bowl top 96 to the top disc 95. Reference is also made to FIG. 8, which illustrates the tubular shaft 94 bearing the fin extensions 105 inserted into the bowl shell 92. Note that the fin extensions 105 extend the spinner vanes to the inner circumference of the bowl shell 92.

In operation, once the separation operation is completed, after the nutrient liquid has been pumped into the bowl of the centrifuge to displace any remaining trypsin, and it is desired to remove the solid cellular material contained within the bowl shell 92, the clamps 121 are released enabling the regulating cover 109, the top cover 108 and the bottom cover 107 to be removed from the apparatus. In addition, the conduit 110 is removed from the bowl assembly 91 thereby enabling one to completely remove the entire bowl assembly from the centrifuge merely by raising it upward. In order to remove the cellular material contained in the bowl assemmbly, a cap is placed over the top of the bowl and the bowl is clamped into a shaker which resuspends the cells. The cap is then removed and the bowl is inverted over a beaker and cell slurry poured out. The live, sterile tissue cells obtained may be stored in a sterile nutrient liquid or may be used immediately.

The present invention offers the following advantages over the prior art.

1. The system reduces manual handling of the tissue and the necessary processing solutions, thereby reducing the possibility of contaminating the tissue cells.

2. The shredding device of the invention not only cuts apart the tissues but also shreds the same so as to maximize the amount of surface area which is exposed to the trypsin solution, enabling much higher yields of tissue cells to be obtained.

3. The improved flow centrifuge design of the invention also enables much higher yields of tissue cells to be obtained due to the fact that the shearing forces to which the cells are subjected during centrifugation have been substantially reduced. It also allows much larger volumes of cell containing fluid to be processed over the prior art.

4. The above advantages can be achieved with minimal human supervision of the equipment, thereby achieving the advantage of substantial automatic operation.

The invention will be further illustrated by reference to the following examples, which are intended to be illustrative and not limiting in nature.

EXAMPLE 1

641,11.5 day chick embryos are passed through the tissue shredder into the trypsinzation vessel, while at the same time, 11.5 liters of medium is pumped through the shredder into the trypsinization vessel. Medium 199 is a well-known medium used to maintain cell cultures for viral propagation. See, for example, *Diagnostic Procedures For Viral and Rickettsial Diseases*, third Edition, Eg. by E. H. Lennette, American Public Health Association, Inc., New York (1964), p. 89. The medium 199 and the shredded tissue are then stirred for 1 minute at 150 RPM. The shredded tissue is allowed to settle to the bottom of the tank for 5 minutes. The medium 199 with suspended red blood cells and debris is pumped out of the vessel at 1300 ml/minute.

10L of tris trypsin of the composition shown below is then pumped into the trypsinization vessel.

| | |
|---|---|
| Sodium Chloride (NaCl), Baker Reagent | 8.0 gm |
| Potassium Chloride (KCl), Baker Reagent | 0.38gm |
| Sodium Phosphate, Dibasic, Anhydrous ($Na_2HPO_4$), Baker Reagent | 0.10gm |
| Dextrose, Baker Reagent | 1.0 gm |
| Tris-Hydroxymethyl Amino Methane (Nutritional Biochemical) [$C_4H_{11}NO_3$] | 3.0 gm |
| Neomycin, C.M. 274 | 0.5 ml |
| Distilled Water | 996 ml |
| Trypsin (GIB), 1:250 Conc. | 2.5 gm |

The trypsin solution is then agitated at 150 RPM and brought to 37° C and the trypsin digestion is carried out for 2 hours. At the end of this time, the fluid containing individual cells is pumped out of the trypsinization vessel and into a flow centrifuge at 500 ml/minute. The centrifuge is operating at 8000 G's. When all of the trypsin solution containing individual cells has passed through the centrifuge, a 1 liter chaser consisting of medium 199 + 10% fetal calf serum is passed through the rotor to displace the trypsin. The rotor is decelerated, removed from the centrifuge and placed in a large shaker. The rotor is vibrated for 1 minute to dislodge the cells from the outside wall and then it is inverted and the concentrated cell slurry is poured off.

EXAMPLE 2

Twenty-five embryos are passed through the tissue shredder into the trypsinization vessel. At the same time, 1.5 liters of medium 199 is pumped through the shredder into the trypsinization vessel. The medium 199 and the shredded tissue is then stirred for 1 minute at 100 RPM. The shredded tissue is allowed to settle to the bottom of the tank for 5 minutes. The medium 199 with suspended red blood cells and debris is pumped out of the vessel.

1.5L of tris trypsin of the same composition as above is then pumped into the trypsinization vessel. The trypsin solution is then agitated at 100 RPM and brought to 37° C and the trypsin digestion is carried out for 2 hours. At the end of 2 hours, the fluid containing the individual cells is pumped out of the trypsinization vessel, through a coarse filter and into a bottle containing 2.5L of medium 199 + 10% fetal calf serum. This is then run against 8L of medium 199 + 10% fetal calf serum using the diaflow method in a sartorius tangential flow filter using 5 micron pads. In this way, the cell suspension is concentrated and the trypsin is diluted out.

While the invention has been shown and described by reference to preferred embodiments, it is to be expressly understood that various changes, modifications and/or substitutions may be made therein without departing from the spirit of the invention. It is the intention, therefore, that the invention be limited only by the scope of the appended claims.

What is claimed is:

1. A closed semi-automated apparatus for producing primary cell suspensions from tissue which includes:
   a shredder device for shredding the tissue;
   a processing vessel adapted for contacting the shredded tissue with an enzyme solution to break down intercellular material thereby freeing tissue cells;
   first inlet means for feeding tissue from the shredder into the processing vessel;
   second inlet means for feeding enzyme into the processing vessel;
   means for separating cells from the enzyme solution and
   a source of nutrient liquid and means for feeding the nutrient liquid to the means for separating cells from the enzyme solution.

2. Apparatus according to claim 1 wherein the second inlet means is located at about the bottom of the processing vessel.

3. Apparatus according to claim 1 additionally including a source of washing liquid and conduit means for feeding the washing liquid into the first inlet means.

4. Apparatus according to claim 3 further including valving means for regulating the feeding of the enzyme solution and the washing liquid.

5. A closed semi-automated apparatus for producing primary cell suspensions from tissue which includes:
   a shredding device for shredding the tissue comprising at least one set of a plurality of movable blade elements and at least a corresponding number of fixed blade elements, the movable blade elements being adapted to be driven through the space defined by adjacent fixed blade elements, wherein the clearance between the movable and fixed blade elements is such that the tissues are shredded;
   a processing vessel adapted for contacting the shredded tissue with an enzyme solution to break down the intercellular material thereby freeing the tissue cells;
   means for separating the cells from the liquid enzyme solution; and
   means for feeding material from the shredding device to the processing vessel, and from the processing vessel to the separating means.

6. Apparatus according to claim 5 wherein the shredder device includes a housing having an inlet and an outlet, at least one rotatable shaft having a plurality of rotary blades fixed thereon, at least a corresponding number of fixed blade elements defining spaces between adjacent fixed blade elements through which the rotary blades may be rotated, and motor means for rotating the shaft.

7. Apparatus according to claim 6 wherein the shredder device is mounted above the processing vessel, whereby the outlet of the shredder device feeds directly into the processing vessel.

8. Apparatus according to claim 1 wherein the means for separating cells from the enzyme solution includes a flow centrifuge with means for centrifugally separating the cells from the liquid enzyme solution without subjecting the cells, during centrifugation, to shearing forces responsible for primary cell damage.

9. Apparatus according to claim 8 wherein the flow centrifuge includes a bowl shell rotatable about an axis, axially disposed inlet means, a cover for the bowl shell and a single outlet means comprising the space defined by the inlet means and the bowl cover.

10. Apparatus according to claim 9 wherein the axially disposed inlet means comprises a tube disposed along the axis, the tube being provided with a plurality of radially-extending spinner vanes at the lowermost portion thereof extending substantially from the tube to the periphery of the bowl shell.

11. Apparatus according to claim 9 wherein the flow centrifuge means further includes a variable speed motor for rotating the bowl shell.

* * * * *